US009468446B2

(12) United States Patent
Kurtz

(10) Patent No.: US 9,468,446 B2
(45) Date of Patent: Oct. 18, 2016

(54) COMBINED MEASURED RESECTION METHODS AND INSTRUMENTS FOR KNEE ARTHROPLASTY

(71) Applicant: William B. Kurtz, Nashville, TN (US)

(72) Inventor: William B. Kurtz, Nashville, TN (US)

(*) Notice: Subject to any disclaimer, the term of this patent is extended or adjusted under 35 U.S.C. 154(b) by 450 days.

(21) Appl. No.: 13/886,235

(22) Filed: May 2, 2013

(65) Prior Publication Data

US 2013/0310838 A1    Nov. 21, 2013

Related U.S. Application Data

(60) Provisional application No. 61/781,521, filed on Mar. 14, 2013, provisional application No. 61/641,875, filed on May 2, 2012.

(51) Int. Cl.
*A61B 17/15* (2006.01)
(52) U.S. Cl.
CPC ........... *A61B 17/151* (2013.01); *A61B 17/154* (2013.01); *A61B 17/155* (2013.01); *A61B 17/157* (2013.01)
(58) Field of Classification Search
CPC .. A61B 17/15; A61B 17/151; A61B 17/154; A61B 17/157
USPC ........................................... 606/86 R, 87–89
See application file for complete search history.

(56) References Cited

U.S. PATENT DOCUMENTS

| | | | |
|---|---|---|---|
| 6,077,270 A * | 6/2000 | Katz | 606/88 |
| 7,329,260 B2 * | 2/2008 | Auger | A61B 17/155 606/88 |
| 7,377,924 B2 * | 5/2008 | Raistrick | A61B 17/154 606/87 |
| 8,167,888 B2 * | 5/2012 | Steffensmeier | 606/88 |
| 2002/0198531 A1 * | 12/2002 | Millard | A61B 17/154 606/87 |
| 2009/0099567 A1 * | 4/2009 | Zajac | A61B 17/155 606/79 |
| 2009/0287216 A1 * | 11/2009 | Warkentine et al. | 606/87 |
| 2010/0087829 A1 * | 4/2010 | Metzger et al. | 606/96 |
| 2010/0331991 A1 * | 12/2010 | Wilkinson et al. | 623/20.32 |

* cited by examiner

*Primary Examiner* — Christopher Beccia
(74) *Attorney, Agent, or Firm* — Brainspark Associates, LLC

(57) ABSTRACT

Described are methods, processes, tools, techniques and/or devices suitable for use in total or partial knee arthroplasty procedures, which can be used to balance the knee and/or allow confirmation of the various gaps in flexion and/or extension prior to resecting the distal and posterior cuts of the femur and/or the resection of the tibia. The various techniques and embodiments described herein may be particularly useful in optimizing and/or reducing the number of resection cuts and/or improper resection cuts made during knee surgery which could result from resecting the knee before balancing.

16 Claims, 15 Drawing Sheets

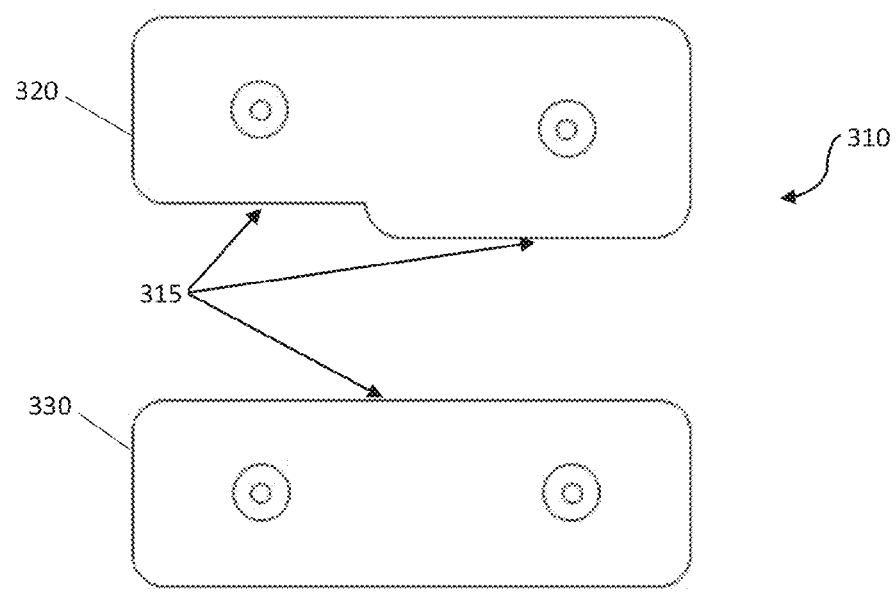
FIG. 7A
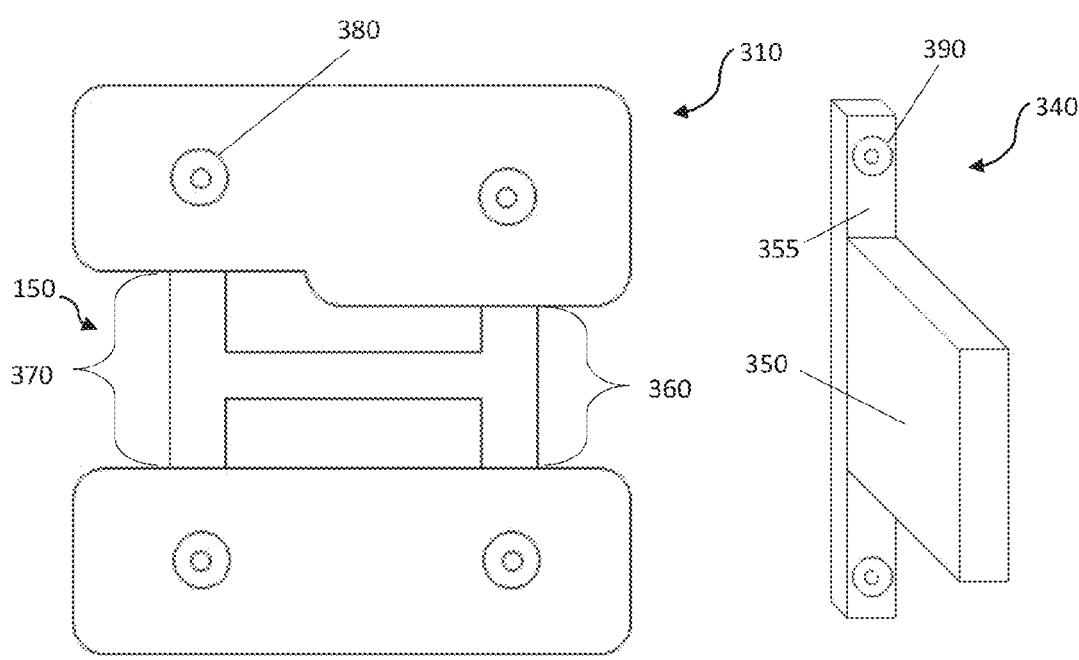
FIG. 7B
FIG. 7C

COMBINED MEASURED RESECTION METHODS AND INSTRUMENTS FOR KNEE ARTHROPLASTY

CROSS-REFERENCE TO OTHER APPLICATIONS

This application claims the benefit of U.S. Provisional Patent Application Ser. No. 61/781,521 entitled "Combined Measured Resection Method for Knee Arthroplasty and Instrument Therefor," filed Mar. 14, 2013 and U.S. Provisional Patent Application Ser. No. 61/641,875 entitled "Combined Measured Resection Method for Knee Arthroplasty and Instrument Therefor," filed May 2, 2012. The disclosure of these documents is incorporated herein by reference in their entireties.

TECHNICAL FIELD

The invention relates to improved and/or patient-adapted gap measuring surgical instruments and related techniques used during total or partial knee arthroplasty.

BACKGROUND OF THE INVENTION

When a patient's knee is severely damaged it may be desirous to repair and/or replace portions or the entirety of the knee with a total or partial knee replacement implant. Knee replacement surgery is a well-tolerated and highly successful procedure that can help relieve pain and restore function in injured and/or severely diseased knee joints.

In a typical knee surgery, the surgeon will expose the knee joint and laterally dislocate the patella. The anterior cruciate ligament may be excised and/or the surgeon may choose to leave the posterior cruciate ligament intact—such soft tissue removal often depends on the surgeon's preference and condition(s) of the ACL/PCL. Various surgical techniques are used to remove the arthritic joint surfaces, and the tibia and femur are typically prepared and/or resected to accept the component artificial implants. Depending upon the surgeon's preference, the component artificial implants should desirably resemble or represent the native thickness of the tibia, femur, articular cartilage, and the menisci to restore the knee to its natural alignment, movement and height.

The resection process involves the assessment of a variety of important "gaps" that the surgeon uses in planning and executing the surgical procedure, which ultimately allows the surgeon to gauge the implant's final rotation, alignment, movement and restoration of height to the joint. One "gap" existing between the tibia and the distal end of the femur is referred to as the "extension gap," and it can include measurement or assessment of the natural gap between the bones and/or other tissues, as well as the space that is created when the bone is resected from one or more of the relevant bone surfaces. Another important "gap" that exists is between the tibia and the posterior end of the femur (when the femur is in flexion) is called the "flexion gap," and it can include measurement or assessment of the natural gap between the bones and/or other tissues, as well as the space that is created when bone is resected from one or more of the relevant bone surfaces. Ideally, the surgeon would prefer the "gap" between the femur and the tibia to be optimized for multiple positions of the femur relative to the tibia (i.e., throughout the entirety of the joint's motion), but a common "approximation" for knee surgery is to attempt to balance the flexion gap and the extension gap of the knee, and assume that the rest of the knee motion will be acceptable during the entirety of the range of motion. Ideally, therefore, the surgeon wants both the extension gap and the flexion gap to be appropriately tensioned when the implant is placed in the joint.

In general, a surgeon does not conduct the balancing of both the flexion gap and the extension gap until some or all the bone resections have been performed. Once the desired bony resection planes have been initially created, the surgeon subsequently utilizes a variety of standard instruments to test the overall implant assembly thickness, such as blocks, spacers, and other tools to ensure proper tensioning, alignment, and rotation. Should the surgeon experience any errors in any of the variables mentioned above, the surgeon may be forced to adjust and/or recut the resection planes in either or both of the femur or tibia. This can result in longer surgery times, lead to malpositioning of implant component(s), improper resection cuts, malalignment of varus/valgus angle(s), and poor axial alignment that may contribute to poor artificial implant positioning, instability of the joint, and poor surgical outcomes. Using such current techniques and surgical tools may contribute to implant component failures and the need for implant revision surgery, prosthetic loosening, arthrofibrosis, deep infection and/or bone loss.

BRIEF SUMMARY OF THE INVENTION

One feature of the invention includes the recognition of a need for a more effective system of surgical instruments and methods to insure a high degree of success in the balancing of the flexion and extension gap, which may in various embodiments include the ability to make part or all of such assessments prior to resecting any of the relevant tibial and femoral surfaces. The disclosed surgical tools and techniques may desirably ensure proper positioning of the artificial joint component assembly, and accurate guiding and cutting of the tibia and femur, which can be important to achieve the most accurate and best fit of the artificial implant components.

The present invention discloses novel surgical instruments, methods and techniques that can be employed by a surgeon in conducting partial knee replacement, total knee replacement, knee revision surgery and/or any surgery required to repair or replace a joint structure. In various alternative embodiments, the features and advantages disclosed herein can be applied with varying utility to surgical procedures for other damaged or diseased articulating joints, such as the ankle, wrist, shoulder, hip, finger, elbow, wrist, toe and/or vertebrae (i.e. intervertebral discs, costovertebral joints, contravertebral joint and/or facet joints).

In one exemplary embodiment, a surgical instrument or tool may be designed to integrate with any commercially available resection jig(s) to measure both the extension and flexion gap prior to resecting the distal end and posterior end of the femur and/or the tibia. The gap measurements can be performed in a variety of leg positions, including one or more of four alignments and locations, such as assessments of the medial extension gap (MEG), the lateral extension gap (LEG), the medial flexion gap (MFG), and the lateral flexion gap (LFG). Data from the various measurements/assessments could impel the surgeon to alter the position of the bone resection jigs and desirably alter a variety of surgical cuts, such as the distal femoral bone cut, the posterior femoral bone cut and/or the tibial planar cuts prior to the cuts actually being made, based off his analysis and/or assessment of the above measurements.

In an alternative embodiment, the surgical instruments or tools may be designed as an independent balancing kit. The balancing kit may comprise (1) a set of surgical instruments and/or tools that measure the gaps in one or more of four or more locations/alignments, including locations such as the medial extension gap (MEG), the lateral extension gap (LEG), the medial flexion gap (MFG), and the lateral flexion gap (LFG); (2) a distal template femur resection block; (3) posterior template femur resection block; and (4) a tibial template resection block. Depending upon component design, the balancing kit could be used in conjunction with any commercially available jigs and/or cutting alignment guides or tools, including tibial bone resection jigs, distal femoral bone resection jigs and/or posterior femoral bone resection jigs.

In various embodiments, the surgical instrument or tools used to measure the various gaps may be designed with fixed heights to match an "expected implant assembly" thickness. An expected implant assembly thickness can include the thickness of an intended joint implant from bone-facing surface of one implant to the bone-facing surface of the opposing joint implant for the opposing bone surface. In one example, this could be the thickness of a knee replacement implant measured from a bone-facing surface of a femoral component to the bone facing surface of the opposing tibial implant. This thickness would typically include the thickness of the femoral implant, the thickness of any poly or other spacer, and the thickness of the tibial tray for a given location on the joint, and this thickness could vary depending upon the location in which it is measured (i.e., the medial and lateral thicknesses of a knee implant could be different). The surgical tool or instrument may come in fixed heights, widths and/or volumes to accommodate the gap measurements that the surgeon wishes to perform. The dimensions of such surgical tools and/or instruments may be analyzed based off the patient's pre-operative range of motion, pre-operative flexion contracture, pre-operative extension lag, pre-operative ligament balancing, pre-operative ligament tension, and/or pre-operative coronal alignment, and then compared to the overall combined thickness of the intended prosthesis (femoral component, polyethylene component, and tibial component).

In another embodiment, the surgical instrument or tools used to measure the various gaps may be designed with height adjustability and/or dimension indicators. The surgical tool and/or instrument may come in a specific design that allows the surgeon to adjust the gap measurements intraoperatively to examine or correct flexion contracture (the inability of a patient to fully straighten their knee joint), coronal mal-alignment (i.e., a varus or valgus knee joint), or other similar degenerative diseases that may require adjustment of a prosthesis and/or its components once the knee is exposed during surgery.

In another embodiment, the surgical instrument of tools used to measure the various gaps may be designed to include patient-specific features and/or surfaces. Various images may be taken preoperatively during the patient's pre-operative range of motion, pre-operative flexion contracture, pre-operative extension lag, pre-operative ligament balancing, pre-operative ligament tension, and/or pre-operative coronal alignment and compared to the overall combined thickness of the intended prosthesis (femoral component, polyethylene component, and tibial component). Using the provided images, the manufacturer may be able to derive a set of specific dimensions and surface contours to design the surgical instrument, tools or kits to balance the knee prior to resecting the relevant tibial and femur surfaces.

BRIEF DESCRIPTION OF THE SEVERAL VIEWS OF THE DRAWINGS

FIG. 7A depicts one embodiment of a commercially available femoral and tibial cutting block;

FIG. 7B depicts one embodiment of a commercially available femoral and tibial cutting block of FIG. 5A with the gap measuring tool of FIG. 3;

FIG. 7C depicts one embodiment of a modular T shaped block that may be secured to any commercially available femoral and tibial cutting blocks;

DETAILED DESCRIPTION OF THE INVENTION

Various features of the present invention may include the employment of a variety of processes, tools and/or devices that can be suitable for use in conjunction with total or partial knee arthroplasty implants, tools and surgical techniques. The various techniques and embodiments described herein may be particularly useful to medical device manufacturers (MDM) and surgeons who may wish to optimize and/or reduce the number of resection cuts or improper resection cuts made during knee surgery due to conducting the balancing of the knee after the bone is resected. This may be accomplished by designing a variety of surgical tools and techniques that facilitates the balancing and/or assessment of the knee prior to resecting the distal and posterior cuts of the femur and the resection of the tibia. Such systems can desirably provide a variety of advantages to the patient, such as (1) improving positioning of implant components due to proper resection cuts; (2) improving coronal alignment of varus/valgus angle(s); (3) improving axial alignment and stability of the joint; (4) improving rotation; and (5) improving patient surgical outcomes.

Derivation of Dimensions to Design the Tools

In one exemplary embodiment, a medical device manufacturer may utilize implant design data from a variety of sources to determine a series of appropriate implant component sizes, designs and/or configurations, which will typically include an intended implant "thickness" or "thickness-range" for each joint replacement implant intended for use in the surgical implantation procedure. The joint replacement implant may be a standard implant, a modular implant and/or a patient-specific or adapted implant, and the thickness measurements may be taken for a variety of component orientations, include flexion and extension of the implant. These thickness or thickness-range measurements may then be used in conjunction with various teaching herein to design one or more implant-specific gap measurement tools appropriate for the surgical procedure. The manufacturer may use choose to employ computer aided systems to design associated surgical instruments and jigs for use with the gap measuring tools.

Figure 1:
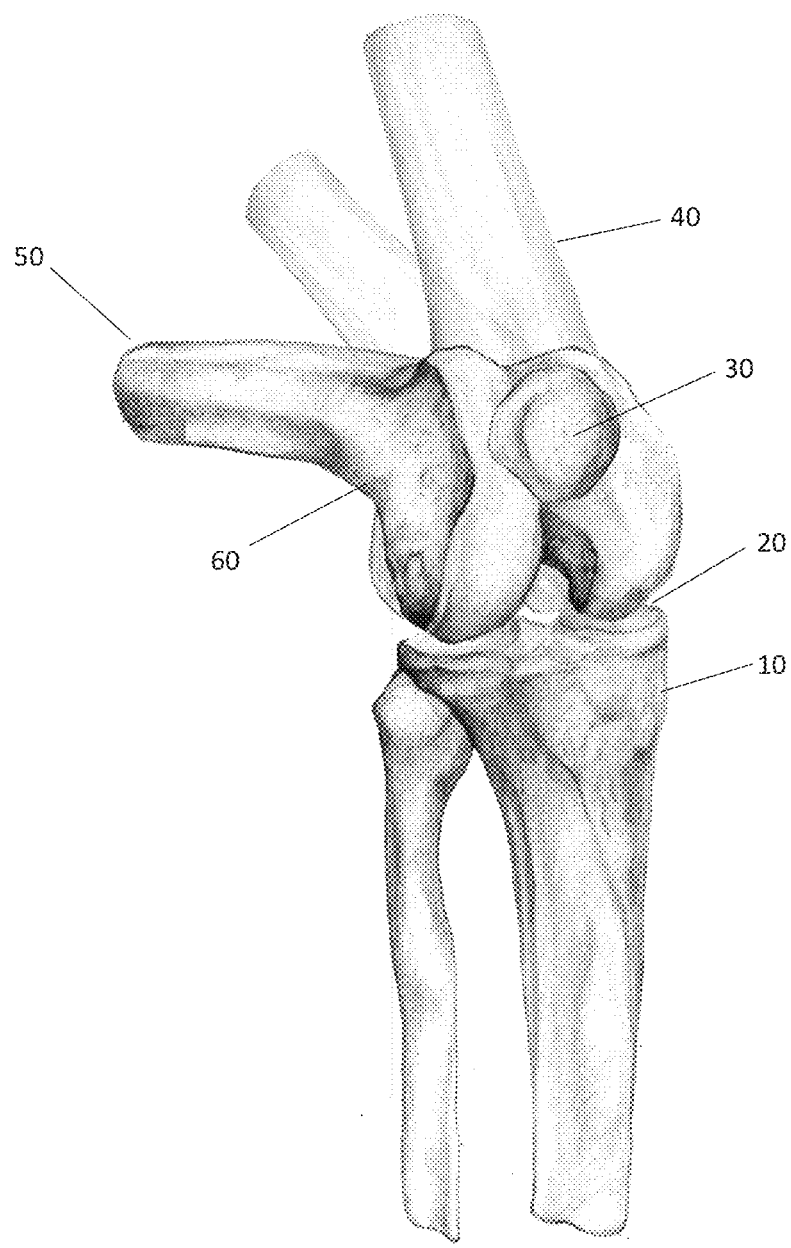
FIG. 1 illustrates a perspective view of an embodiment of a human knee undergoing flexion through extension.

In one exemplary embodiment, the medical device manufacturer may derive measurements from a patients' pre-operative surgical work-up or from a database library to design fixed gap measurement tools for use in the surgical procedure. FIG. 1 illustrates a perspective view of one embodiment of a human knee undergoing movement from a flexed orientation 50 through and extended orientation 40. Depending upon the manufacturer's needs, the manufacturer may request that a surgeon collect a variety of patient images of the patient's femur 60, tibia 10, and patella 30 during a patient's pre-operative range of motion, which could include structural images and/or data as well as motion and/or soft-tissue related data such as pre-operative flexion contracture, pre-operative extension lag, pre-operative ligament balancing, pre-operative ligament tension, and/or pre-operative coronal alignment. The surgeon then may collect and record specific measurement data from the images and transmit them to the manufacturer. The manufacturer can use this information to design specific implants and/or tools for the patient, select a set of tools for the patient, or create kits that a surgeon may use during knee surgery. Alternatively, the manufacturer may derive the dimensions of the gap measuring tools from a variety of standard database library that stores data with similar pre-operative ranges of motion for healthy patients, diseased patients, and/or a combination thereof. The manufacturer may use the data obtained from the surgeon or the library and use statistical analysis to design the implant, tools and/or instruments.

In alternative embodiments, the medical device manufacturer may derive measurements from a variety of pre-operative images to design patient-specific gap measurement tools needed for surgery. The manufacture may request that the surgeon obtain one or more of a variety of pre-operative images of a patient as the patient's knee is adjusted throughout a given range of motion (as discussed above), and transmit these images to the manufacturer. The manufacturer can then utilize computer aided design, if desired, to use the 2D, 3D, and/or "2D into 3D" (i.e., "converted" image data) images to recreate the movement and/or anatomical features of the patient's femur 60 and/or tibia 10, while undergoing flexion 50 and/or extension 40. The manufacturer can derive measurements from the images to design appropriate surgical instruments and tools needed, which may include tools having patient-specific surfaces or contours to be easily positioned on arthritic knee anterior surfaces. The manufacturer may similarly choose to design implant components, including patient specific implant components, using the same image data.

Figure 2A:
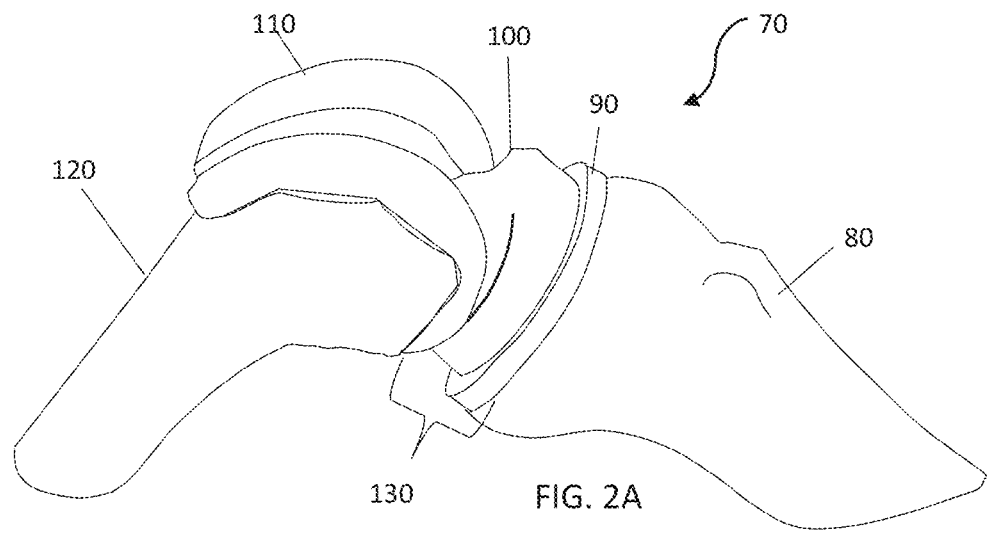
FIG. 2A illustrates a perspective view of an embodiment of a human bone model with an total knee assembly prosthesis in flexion.
Figure 2B:
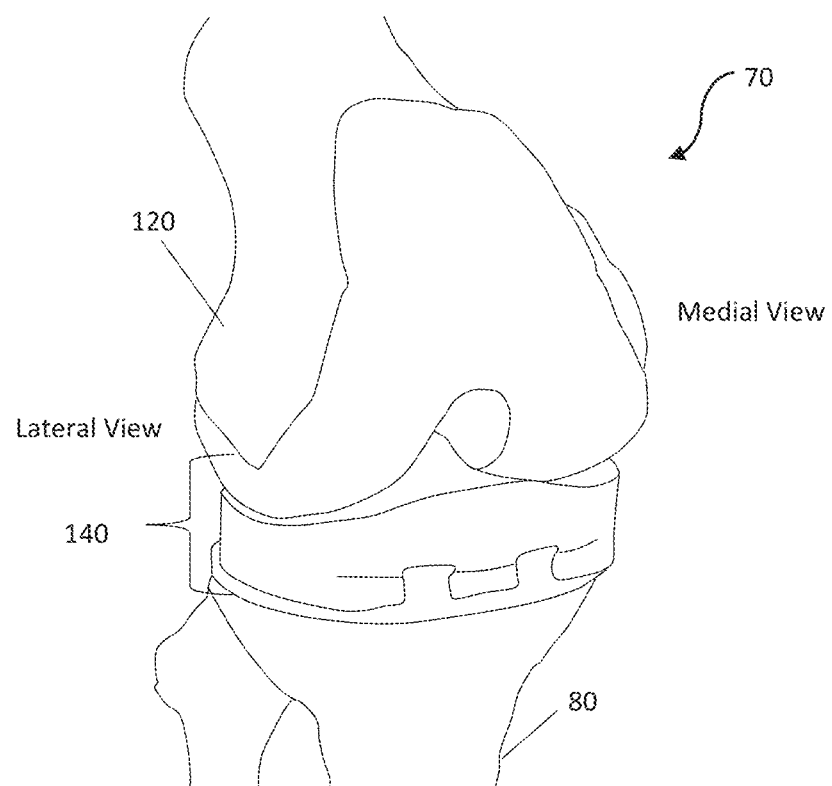
FIG. 2B illustrates a perspective view of an embodiment of a human bone model with an total knee assembly prosthesis in extension.

In another embodiment, the manufacturer or surgeon may match or verify the designed gap measurement tool dimensions by conducting a verification process. The verification process may include a comparison of the designed gap measurement tool to the prototypes of a patient-specific implant prosthesis or any standard commercially available prosthetics to measure the combined thickness of the intended prosthesis assembly 70, which typically includes a femoral component 110, a polyethylene or "spacer" component 100, and a tibial component 90, such as the implant shown in FIGS. 2A and 2B. Since manufacturers will often vary the design and selected material thicknesses of the femoral implant component 110 and/or polyethylene component 100 thicknesses depending upon the rotation angle of the implant (i.e., the overall or composite implant thickness may change depending how the femoral component sits on the tibial components), it may be advantageous to measure any changes in thickness in the prosthetic assembly in both extension 140 (such as shown in FIG. 2B) and in flexion 130 (such as shown in FIG. 2A) to identify any relevant thickness variations in the implant. Also, it may be desirable to create prototypes of the gap measurement surgical instrument or kits and proceed to verify recommended surgical cuts for surgical planning or strategies to ensure that no further design changes are necessary or warranted. Where poly inserts or other modular components having differing sizes and/or thicknesses (or having non-uniform surface features and/or thicknesses) are included with an implant, the various gap measuring tools may similarly be provided in varying sizes and/or thicknesses corresponding to the various modular options available.

Surgical Tools, Instruments, and or Kits

Figure 3:
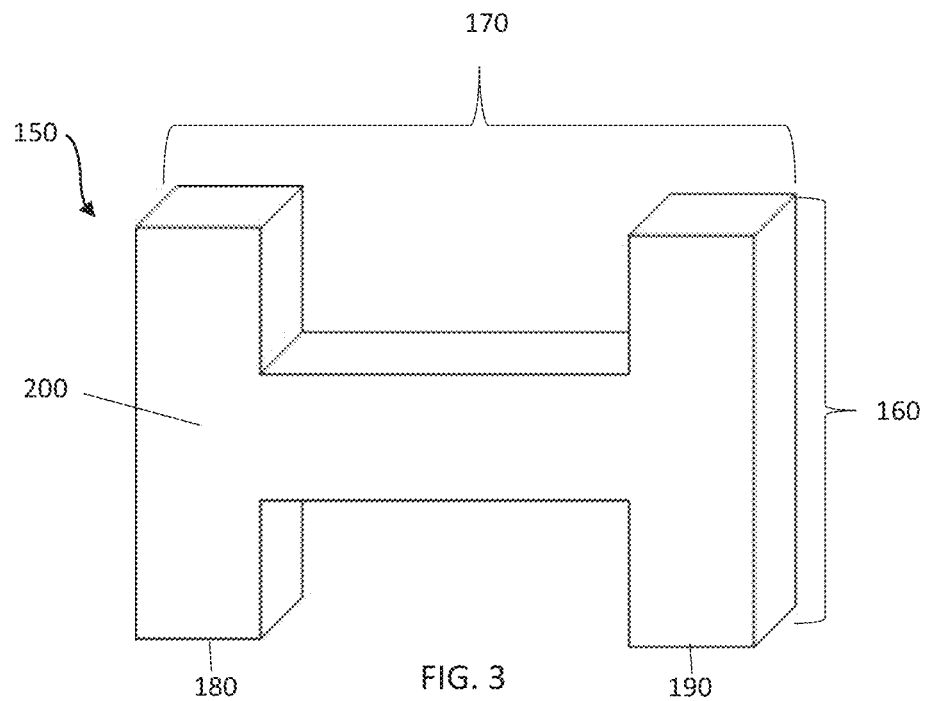
FIG. 3 depicts a perspective view of one embodiment of an "H" shaped gap measuring tool.
Figure 4:
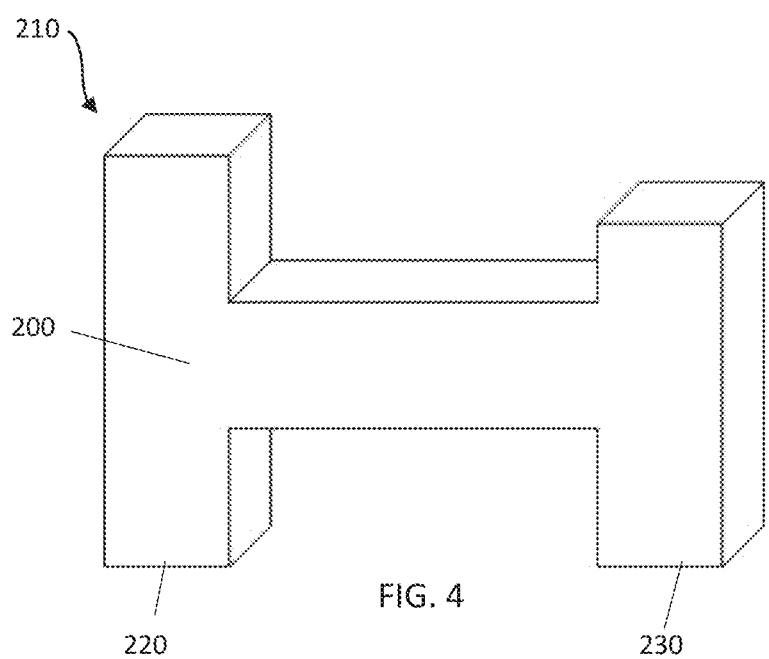
FIG. 4 depicts a perspective view of an alternative embodiment of an "H" shaped gap measuring tool.

FIG. 3 depicts a perspective view of one embodiment of an "H" shaped gap measuring tool 150 having equal medial 180 and lateral sections 190 of equal heights. This tool 150 may be designed to have a desired fixed height 160 or heights, which in various embodiments will simulate or reflect various anatomical measurements (relating to resection and/or implant component thickness measurements) for the patient relative to an anticipated and/or desired range of motion and joint kinematics. The thickness measurements can be obtained from patient-specific pre-operative data, from a database library, and/or from structural and/or performance data of the desired implant prosthetic assembly (i.e., thickness measurements of the femoral component, tibial component and/or the polyethylene component), which could include the use of any standard and/or patient-specific images. The width 170 of the tool 150 could be fixed and/or variable and derived using a variety of methods, including the use of the measurements of various commercially available femoral and tibial cutting blocks, templates, and guides, as well as measuring the tibia and femoral width (i.e., a not to exceed width), or any standard and/or patient-specific measurements that may be used during the surgical procedure. In one alternative embodiment shown in FIG. 4, an offset H shaped gap measuring tool 210 could be designed having offset medial 220 and lateral 230 heights. The offset shape may be particularly useful in assessing and/or correcting undesired, damaged and/or malformed joint anatomy, such as where the tool can accommodate a patient's coronal mal-alignment, as well as other types of mal-alignment that a patient may exhibit.

If desired, the tool could comprise an equal or offset H shaped gap measuring tool, with surfaces 200 that can contact or abut various anatomical surfaces of the patient's joint, which could include designing one or more anterior/posterior tool surfaces as a standard substantially conforming shape, an approximate shape or some patient specific contoured shape. Also, the described H-shape should not be interpreted as a critical or limiting feature, as various other shapes and/or sizes for the tool maybe desirable.

In the various embodiments described herein, the height of the medial and lateral portions of the H block (see FIGS. 3 and 4) could reflect medial extension gap (MEG) and/or lateral extension gap (LEG) variations due to anatomical variation as well as variation on height due to thickness variations in the combined implant thickness, if such varied between the medial and lateral sides of the implant.

Figure 5:
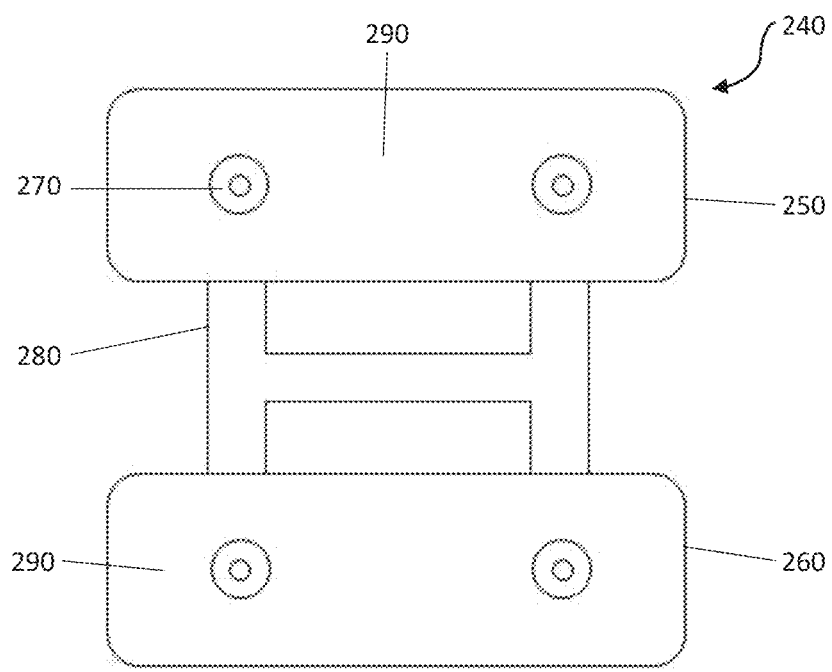
FIG. 5 depicts a front view of an embodiment of a modular gap measuring tool assembly.
Figure 6:
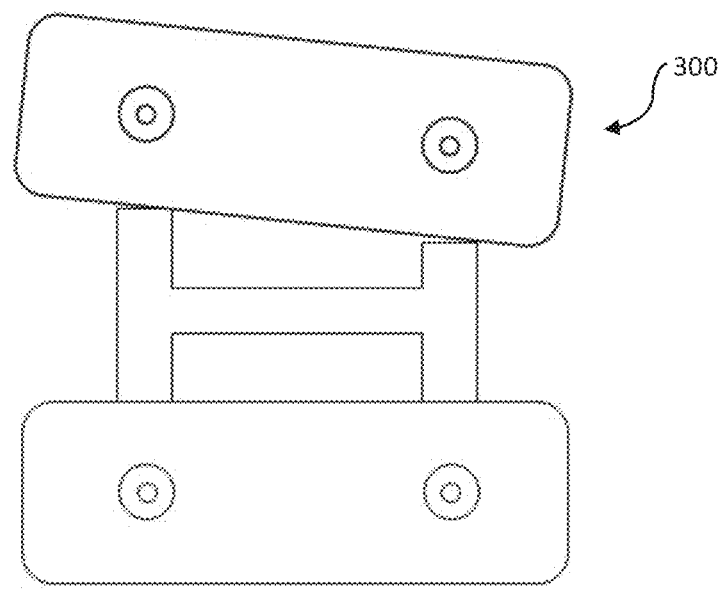
FIG. 6 depicts a front view of an embodiment of a modular gap measuring tool assembly of FIG. 3 tilted to correct coronal mal-alignment.

FIG. 5 depicts a front view of an embodiment of a modular gap measuring tool assembly 240. The gap measuring tool assembly may be provided or integrated in a kit or may be sold independently with fixed sizes based on implant manufacturers implant assembly thicknesses. The modular assembly may include a femoral block 250, a tibial block 260, and a gap block 280. The femoral block 250 and the tibial block 260 may comprise portions of pre-existing surgical tools such as resection guides, or these blocks may be designed and manufactured solely for balancing the knee joint, and formed in standard shapes and/or sizes or may mimic the patient's anatomy for the various tibial bone cutting blocks or templates, the distal femoral bone cutting block or templates, and/or the posterior femoral bone cutting block or templates. The femoral block 250 and the tibial block 260 may include counterbores 270 or other features (i.e., openings and/or recesses) to accommodate and/or position one or both blocks on the anterior or other surface(s) of the tibia and femur. Alternatively, the gap block 280 may be pinned or otherwise attached one or both of the tibial or femoral cutting blocks. Standard pins that are used during surgery to position cutting guides and/or templates (as well as attach other tools to the joint anatomy or indicate various locations on the joint) may be used to position the gap measuring tool assembly 240. Once the femoral block and tibial block are in a desired position and/or orientation, the gap block 280 may be inserted between the blocks (see the configuration of FIG. 5), or various combinations of blocks can be connected and used, such as where it may be desirous to integrate all three pieces together into one fixed piece.

In one alternative embodiment, an offset modular measuring tool assembly 300 could be designed and used to correct coronal mal-alignment, and desirably to ensure that the ultimate prosthesis assembly is positioned properly within the joint.

In various embodiments, it may be desirous to remove the gap block 280 from the femoral and tibial blocks 250 and 260 after measuring and/or assessing the proper gaps and/or adjusting the femoral block 250 and/or tibial block 260, as the surgeon may employ various surfaces or other features of the femoral block 250 and/or tibial block 260 as guides or jigs to resect the surfaces (which could obviate a need for further swapping or changing of tools or jigs, if desired).

FIG. 7A depicts a front plan view of one embodiment of commercially available femoral and tibial cutting blocks 310. These block 310 will desirably include a surface 315 or other feature that can accommodate a corresponding surface of an H shaped gap measurement block, such as that depicted in FIG. 3 could be used. Of course, alternative measuring tool designs incorporating shim blocks or other measuring tools of various sizes, shapes and/or configurations could be created in a similar manner to fit within and/or between standard commercially available tibial and femoral bone cutting blocks or templates, which could include distal femoral cutting blocks as well as posterior femoral cutting blocks. Various embodiments of a gap measuring block 150 may be introduced, positioned and secured (if desired) prior to taking any gap measurements, such as that shown in FIG. 7B. Alternatively, a single T shaped gap measurement block 340, such as shown in FIG. 7C, could be designed to include a 350 shim block that slides into and/or between the medial 360 and/or the lateral 370 side of the commercially available femoral and tibial cutting block 310, align with the block counterbores 380 with the T shaped gap measurement tool counterbores 390, and facilitate the assessment and securement or pinning of one or more of the blocks to the underlying bony anatomy using standard, supplied pins, or uniquely designed pins to secure them while undergoing the balancing technique prior to resection. Alternatively, the gap block 280 could be pinned or otherwise secured to at least one of the tibial or femoral cutting blocks.

The T-shaped design can also includes a stop feature 355 which desirably acts as a positive stop to prevent the surgeon from inserting the T-shaped gap measurement tool too far between the relevant block surfaces. If desired, a pair of such T-shaped blocks could be used to balance and/or assess the knee, with one side of teach T-block having a first or second thickness to measure the flexion of the knee in a first orientation (i.e., use the first and second blocks in one orientation to assess the medial and lateral flexion gaps, respectively), and then another side of the T-shaped blocks (i.e., rotating or turning the block 90 degrees) having a third and fourth thickness to measure the extension of the knee in a second orientation (i.e., use the first and second blocks in a second orientation to assess the medial and lateral extension gaps, respectively). If desired, the flat surfaces of the T-shaped blocks could rest along the flat surfaces of the tibial and femoral blocks (320 and 330) and ensure that the tibial and femoral blocks were perpendicular for the flexion and extension measurements and thereby ensure that the knee was in 90 degrees of flexion and 0 degrees of flexion respectively. The figures depict measurements being taken at 0 and 90 degrees of flexion, but the blocks could be configured to take measurements multiple degrees of flexion like 0, 10, 20, 30, 40, 50, 60, 70, 80, 90, 100, 110 or 120 degrees of flexion by allowing multiple reference lines or multiple blocks for each degree of flexion.

Figure 8A:
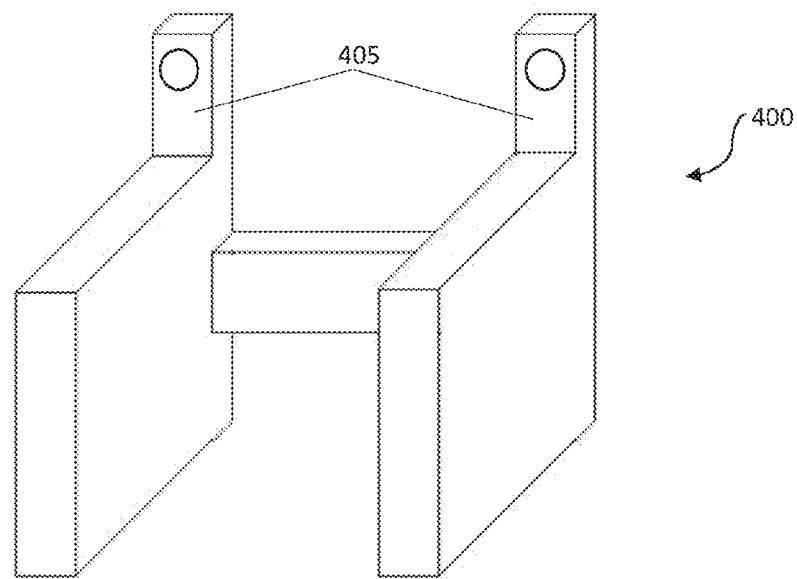
FIG. 8A depicts an alternative embodiment of an "L" shaped gap measuring tool.
Figure 8B:
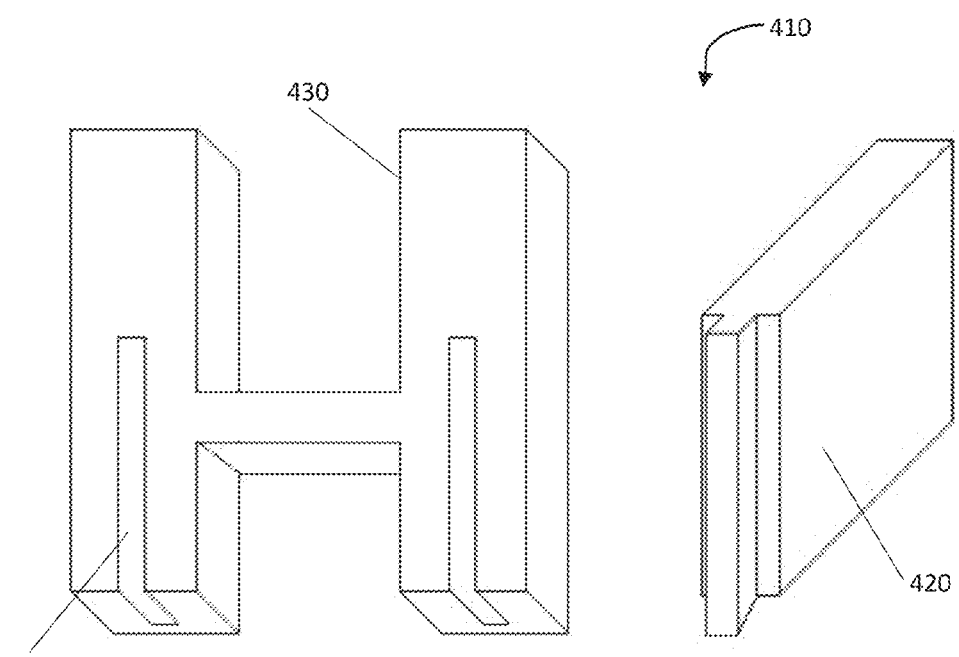
FIG. 8B depicts an alternative embodiment of an modular "L" shaped gap measuring tool.

FIG. 8A depicts an alternative embodiment of a one-piece "L" shaped gap measuring tool 400. This gap measuring tool may be designed as one-piece design that integrates a gap measuring block and one or more fixation legs 405. The gap measuring block can be designed in accordance with the various teaching and methods described herein. The fixation leg 405 could be used to fixate the L shaped gap measuring block to any standard commercially available tibial and or femoral cutting block and/or templates. The fixation leg can also be used as a positive stop to prevent the surgeon from inserting the block too far into the joint. Different sizes of the one-piece L shaped gap measuring tool 400 may be available. In an alternative embodiment, the L shaped block may be modular. FIG. 8B depicts an alternative embodiment of a modular "L" shaped gap measuring tool 410 that may comprise a frame 430 and a gap shim block 420. The frame may be designed with a channel 440 that may accommodate the gap shim block 420 and be securely tightened. The frame 430 may also be designed with counterbores (not shown) to allow it to be pinned to any commercially available tibial and/or femoral cutting blocks and be used as a positive stop.

Figure 9A:
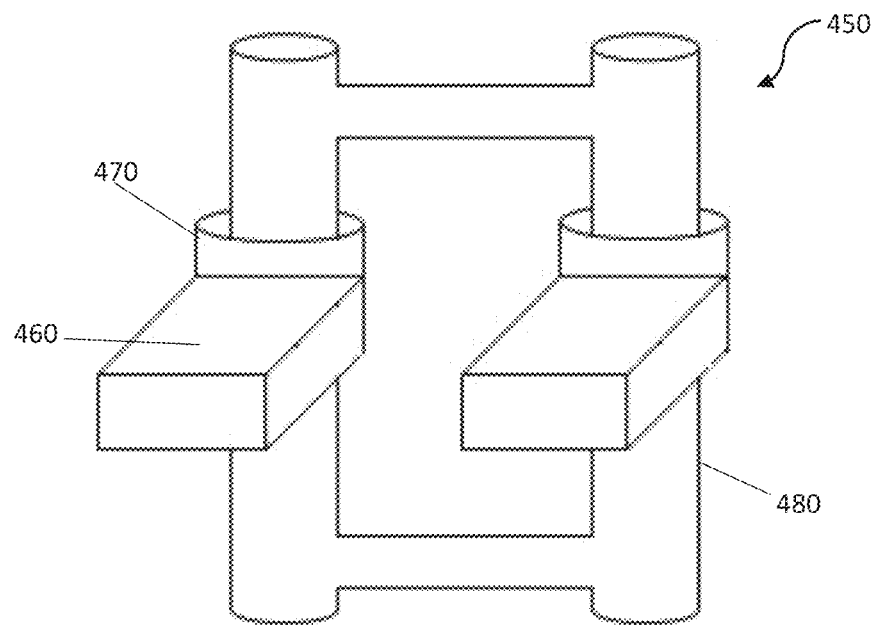
FIG. 9A depicts an alternative embodiment of an adjustable gap measuring tool.

FIG. 9A depicts an alternative embodiment of an adjustable gap measuring tool 450. The adjustable gap measuring tool may comprise connectively removable collars 470, with a shim block 460, and a frame 480. The removable collars may be secured to the frame and released to slide along the frame 480 for maximum adjustability. The adjustability of the shim blocks can give the surgeon increased flexibility in taking thickness measurements and/or performing assessments of the intended knee prosthesis during surgery, and allow him/her to adjust the shim block to a desired height. The entire adjustable gap measuring tool (with the height secured, if desired) could be placed in between commercially available femoral and tibial cutting blocks, or may be pinned using similar counterbores 500 (see FIG. 9B) to those that are available on various designs of commercially available blocks.

Figure 9B:
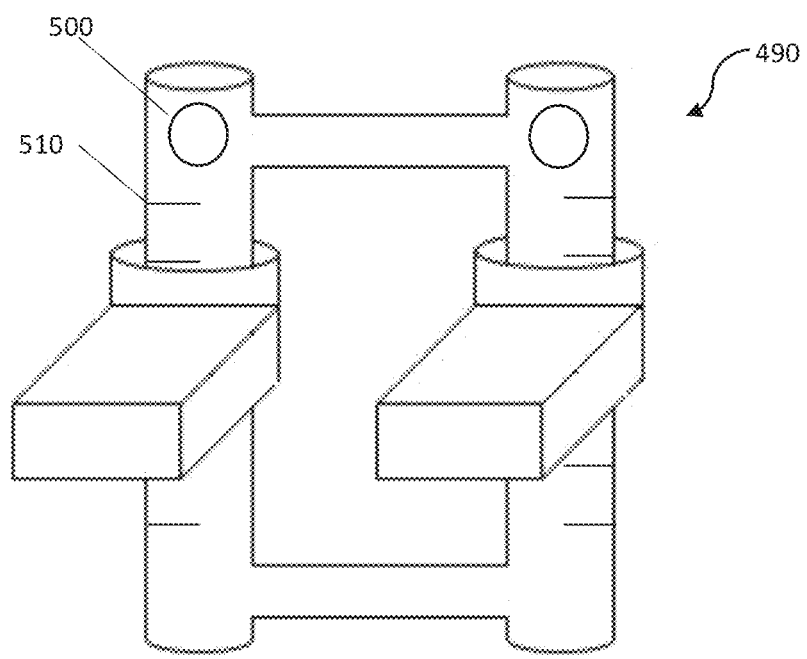
FIG. 9B depicts an alternative embodiment of an adjustable gap measuring tool of FIG. 9A with scaled measurements.

FIG. 9B depicts one alternative embodiment of an adjustable gap measuring tool of FIG. 9A with scaled measurements. The scaled measurements may assist with using the adjustable gap measuring tool 490 in a manner similar to a set of calipers. The adjustable gap measuring tool may be used to measure the thickness of the intended knee implant and/or the guiding cut blocks, and then manually adjusted to a desired height. The adjustable gap measuring tool may be placed or positioned and can be placed in between commercially available femoral and tibial cutting blocks, or may be pinned using the same counterbores 500 (see FIG. 9B) that are on the commercially available blocks. Alternatively, all of the gap measurement tools contemplated herein, may be designed with multiple sets of pin holes that allow the blocks to translate a set amount to vary the thickness of the cuts. The surgeon could move one, two or all three blocks without moving the pins by selecting a slightly translated set of pin holes until all the measurements worked out to the desired thickness and/or desired balancing/kinematics of the knee joint.

If desired, the adjustable gap measuring tool could incorporate a graduated scale such that the surgeon could position and/or adjust the blocks to eventually alter the bone cuts, such as a situation where the surgeon desires to remove more bone where it is anticipated or determined that the patient had insufficient preoperative motion in the preoperative joint. The graduated scale could show the preferred measurement for a "loose" knee and for a "tight" knee. The "tight" knee could be a slightly greater distance that desired post-operatively, which would correspond to a possible increase in the depth of bone resection (to "loosen" the knee) and possibly improved post op range of motion. If the surgeon felt the patient's knee was tight in both flexion and extension before surgery, then the surgeon could position the blocks such that the graduate scale lined up with the "tight" knee markings in the medial extension gap (MEG), lateral extension gap (LEG), medial flexion gap (MFG), and lateral flexion gap (LFG). If the surgeon felt the patient's knee was loose before surgery (full range of motion), then the surgeon could position the blocks such that the graduate scale lined up with the "loose" knee marking in the MEG, LEG, MFG, and LFG. The surgeon could try to match the extension marking with the flexion markings as well as to try to match both the extension and flexion markings with the preoperative patient factors.

In an alternative embodiment, the gap measuring tool may also be designed as shim type blocks (not shown). The shim type blocks may be designed as a set of various heights and sizes, or may be designed as stackable (i.e. successive layers of material and/or containers within containers) to increase height. Shim blocks may be used in conjunction with any of the embodiments disclosed herein.

In the embodiments disclosed herein, the gap measuring tools may be designed with a wide variety of materials. The materials may include, but are not limited to, any polymer, metal, or a combination of thereof. Further, the selection of material may take into consideration any sterilization needs of the product and the use of the device.

Surgical Methods or Techniques

In one exemplary embodiment, the surgeon may wish to balance and/or measure the proposed spacing between the femoral resection blocks and/or the tibial resection blocks (which will desirably control the proposed surgical resection planes on one or both of the bones) prior to making an initial resection on the bones. The surgeon will obtain a desired gap measuring tool. The measuring tool may be provided in the implant kit, may be sold independently in an assembly, and/or may be includes with a patient specific implant or incorporate patient-specific features. The measuring tool may be designed to integrate between various designs of distal femoral cutting block (DFCB), the anterior/posterior femoral cutting block (APFCB) and/or the tibial cutting blocks (TCB), or could be designed as part of an independent measuring and/or resection guide assembly.

Desirably, the surgeon will expose the knee joint in a desired fashion and position a tibial jig or tibial cutting block (TCB) in an appropriate position on the tibia based on the surgeon's experience and/or preference, or if a patient-specific jig is being used, off the fit of the tibial jig with the superior and/or anterior surface of the tibial bone. The surgeon may then position a femoral jig or distal femoral cutting block (DFCB) in a similar manner on the femur, which could include positioning of the jig on a femoral location based on experience and/or in a desired and/or an appropriate position based off the fit of a patient specific femoral jig to the surface(s) of the femoral bone (osteophytes, cartilage surfaces, and/or subchondral bone). The tibial jig and the distal femoral jig could be pinned in place to their respective bones to ensure the jig positions did not move relative to the underlying anatomical structures to which they are attached. The tibial jig or the femoral jig may be patient specific and/or commercially available jigs and/or blocks for one-piece and/or modular implant systems.

Once the jigs are pinned to their respective bones, the surgeon can then use one or more gap measuring blocks as described herein to assess the soft tissue tension/laxity and gap distance across the joint as described herein. In the described embodiment, the extension gap is the first gap assessed, followed by assessment of the flexion gap (which may be accomplish using the same jigs or by different femoral and/or tibial jigs and associated spacer blocks, as desired). Various alternative embodiments could be employed to measure the flexion gap first, as well as embodiments to assess gaps in various other degrees of flexion and/or extension of the joint (i.e., 15 degrees of flexion, 30 degrees of flexion, 45 degrees of flexion, 75 degrees of flexion, 115 degrees of flexion, etc). Desirably, the surgeon can use the various gap measurement tools disclosed herein to verify the distances between the medial and lateral compartments of the knee for one or both of the extension gap and/or the flexion gap. In one exemplary embodiment, the gap distances or measurements can correspond to one of four distinct measurement: the medial extension gap (MEG), the lateral extension gap (LEG), the medial flexion gap (MFG), and the lateral flexion gap (LFG). In various embodiments, these measurements can be made as close to the center of the respective femoral condyle (i.e., medial and/or lateral) as possible.

Figure 10:
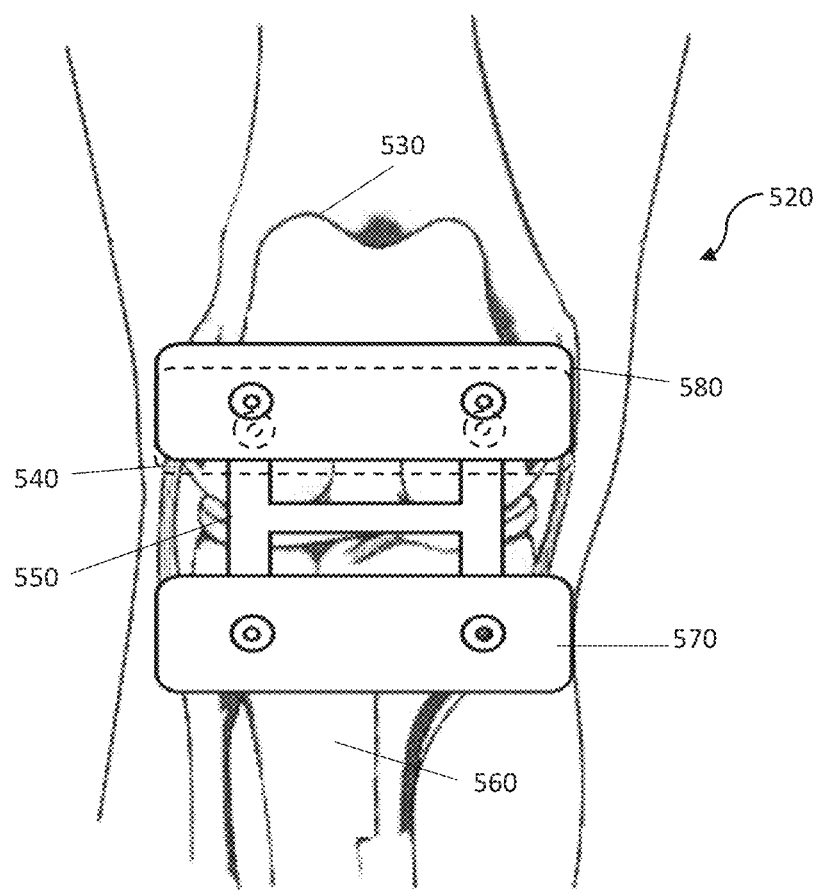
FIG. 10 depicts an anterior view of an modular gap measuring tool assembly of FIG. 5 positioned on the human knee prior to resecting the distal femur bone and tibial bone surfaces.

In the exemplary embodiment, the surgeon may first decide to position the knee in extension 520 (i.e. extend the knee to 0 degrees) and verify and assess the medial extension gap (MEG) and the lateral extension gap (LEG), as shown in FIG. 10. Because the femoral and tibial jigs 580 and 570 extend outward from the front of the knee (see FIG. 11), it is not necessary to insert the gap measurement tool 550 between the articulating surfaces of the femur and tibia to assess the joint. Rather, the surgeon will insert the appropriate gap measurement tool 550 between (or it may already be attached to) the intended DFCB 580 that is attached to the femur 530 and the intended TCB 570 that is attached to the tibia 560 to measure the proper distance and joint balance. If the anticipated thickness of the bone removed by the proposed cuts (and proposed resection planes created thereby) does not correspond with the desired alignment and/or soft tissue tension/laxity of the knee, then the surgeon can change the position 540 of one or more of the cutting blocks before any resection cuts are made. If the position, orientation and thicknesses of the proposed cuts are confirmed as appropriate by the surgeon, the surgeon may make the corresponding resection cuts.

Figure 12:
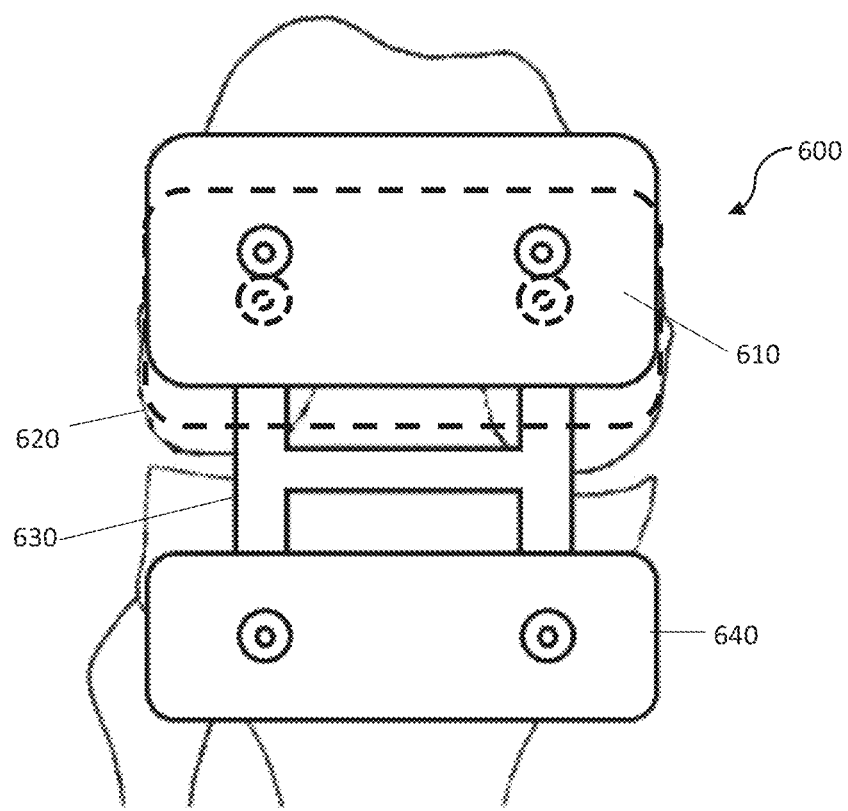
FIG. 12 depicts an anterior view of a modular gap measure tool assembly positioned on the human knee prior to resecting the posterior bone and tibial bone surfaces.

In various embodiments, such as shown in FIG. 12, the surgeon may subsequently position the knee in flexion 600 (i.e. flex the knee to approximately 90 degrees) to verify and assess the medial flexion gap (MFG) and the lateral flexion gap (LFG). Once appropriate cutting blocks or guides are positioned and secured to the appropriate bones (which in the case of the femoral block may necessitate a different cutting guide that for the flexion assessment), the surgeon may insert the appropriate gap measurement tool 610 between or attached to the intended APFCB 610 and the intended TCB 640 to measure and assess the distance and joint balance. The APFCB can be attached to the femur through drill pins—if desired, the surgeon could measure the distance between the pins and the TCB with the appropriate gap measurement tool instead using the APFCB. With the gap measuring tool in place, the surgeon can manipulate the knee and determine if the tension/laxity of the soft tissues is an appropriate amount and whether the varus/valgus tilt and/or other alignments of the knee is appropriate. If the surgeon wishes to alter the proposed alignment, or if the anticipated thickness of the bone removed by the proposed cuts does not create a properly balanced knee in the proposed alignment, then the surgeon can change the position of one or more of the cutting blocks to a new location and/or orientation (i.e., the APFBC and/or TCB can be moved and/or rotated, and then repinned, if desired), and can reassess the knee before the cuts are made 620. Once the position, orientation and thicknesses of the proposed cuts are confirmed by the surgeon, the surgeon may make one or more of the corresponding resection cuts, if desired, or the anatomy may be retained.

The various teachings disclosed herein enable a surgeon to assess the knee in both flexion and extension prior to making any bone cuts, as well as to choose to make the cuts after any individual assessment are made. If desired, once a resected surface has been created, the surgeon may use that surface for subsequent assessments, and/or may employ alternative measuring tools that reference the cut surface in some manner. In addition, the cuts may be made in various knee orientations, depending upon the surgeon's preference).

By avoiding resection of bone surfaces prior to conducting a complete assessment of the patient's knee, the surgeon can retain significantly flexibility in his or her surgical options. Using the teachings provided herein, where balancing and assessment of a knee indicates an undesirable condition may exist, the surgeon can choose to adjust one or more bone resection guides to accommodate and/or correct the condition. For example, where assessment indicates the knee is too tight in both flexion and extension, it may be desirous to increase the resection depth of the tibia, thereby potentially loosening the knee in both flexion and extension. However, where the knee is tight in flexion but acceptable in extension, it may be desirous to manipulate only the posterior cut on the femur. Similarly, a knee that is too tight in extension but acceptable in flexion may necessitate alteration of the distal femoral cut. With appropriate assessment of the knee, the need for soft tissue releases and/or tibial inserts of differing sizes may be reduced and/or obviated.

Figure 11:
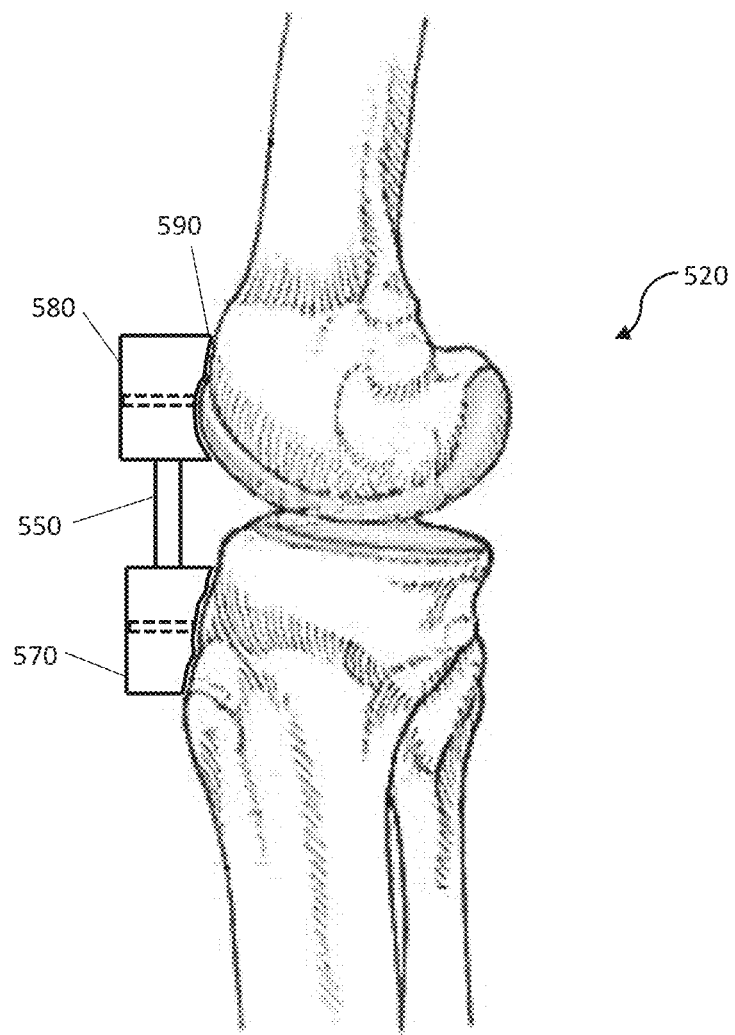
FIG. 11 depicts a lateral view of a modular gap measure tool assembly of FIG. 5 with patient specific surfaces positioned on the human knee prior to resecting the distal femoral bone and tibial bone surfaces.

In various embodiments, a surgeon may view or take measurements using the gap measurement tool 550 along a lateral view, such as shown in FIG. 11. In this embodiment, the gap measurement tool may positioned between the DFCB 580 and the TCB, or it may comprise a unitary or two-piece assembly with optional patient specific surfaces 590 to be pinned where the intended resection blocks will be placed.

In another embodiment, the surgeon may use an adjustable gap measurement tool to obtain one or more of the assessments of the medial extension gap (MEG), the lateral extension gap (LEG), the medial flexion gap (MFG), and the lateral flexion gap (LFG). The EGMB might have a range of measurements or scale depending on the patient's pre-operative range of motion. The EGMB could have a scale on the top of the medial and lateral bar for a stiff knee and a loose knee. The corresponding mark on the scale for a loose knee might remove less bone than the corresponding mark on the scale for a tight knee. Using various embodiments described herein, a surgeon could decide pre-operatively how loose or tight he or she felt the patient's knee replacement needed to be based off the patient's range of motion. The surgeon could then try to ensure that the four measurements (MEG, LEG, MFG, and LFG) were each optimized, or corresponded to a same point on a given assessment or flexibility scale, or reached an average or other desired/acceptable point that could be selected at the surgeon's option.

Figure 13:
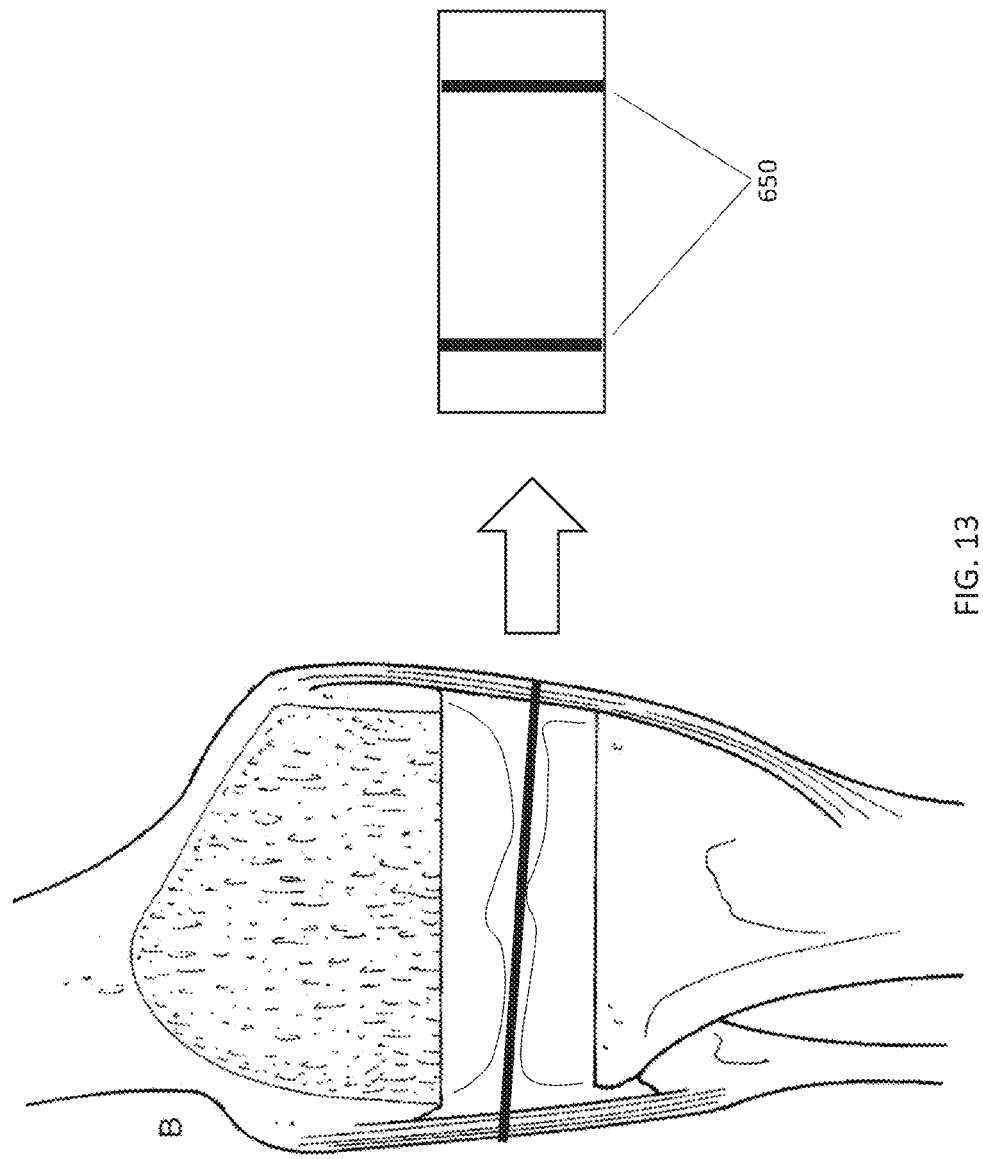
FIG. 13 depicts an embodiment of a knee joint having a pre-operative neutral alignment.
Figure 15:
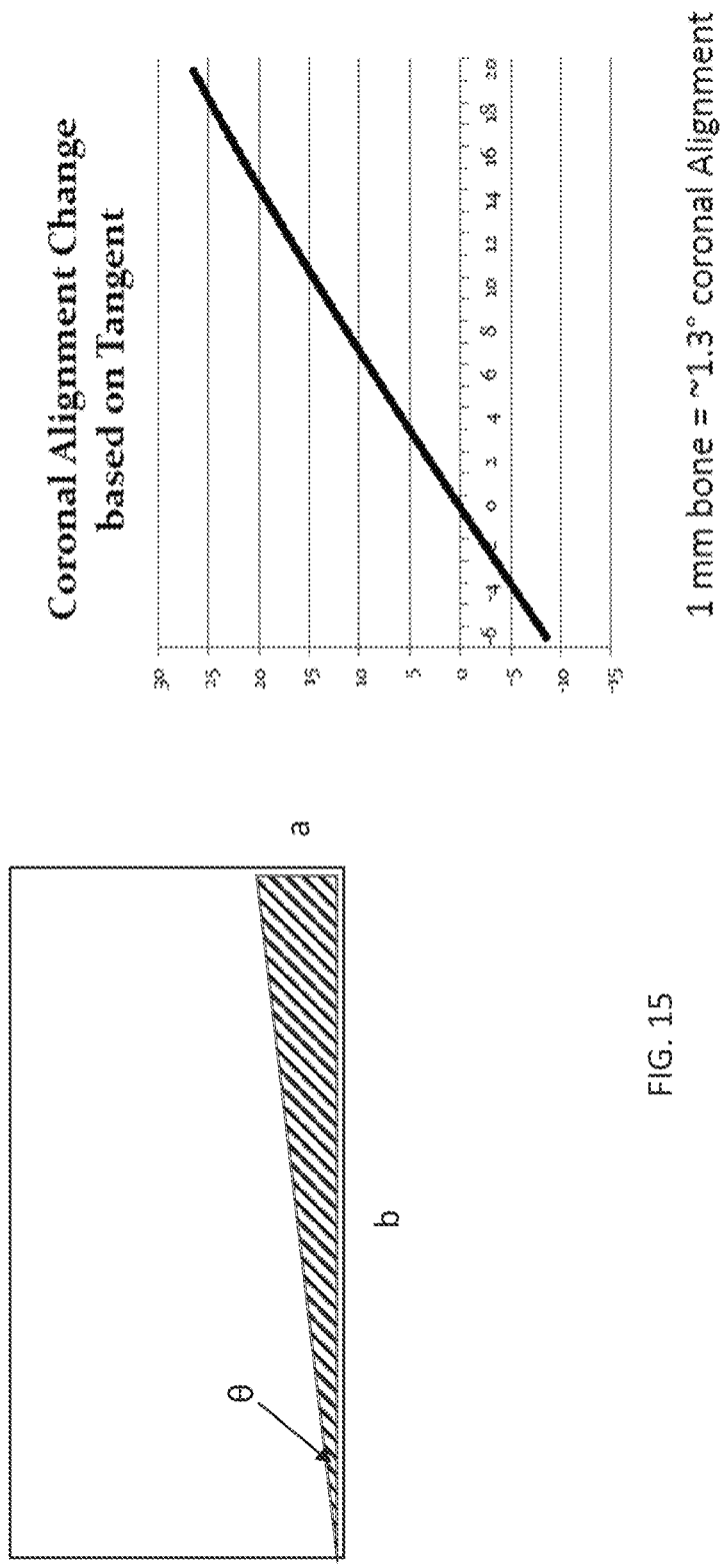
FIGS. 15-17 illustrate graphical representations of alterations in coronal alignment and various medial and lateral gap measurements, differences and modifications.
Figure 16:
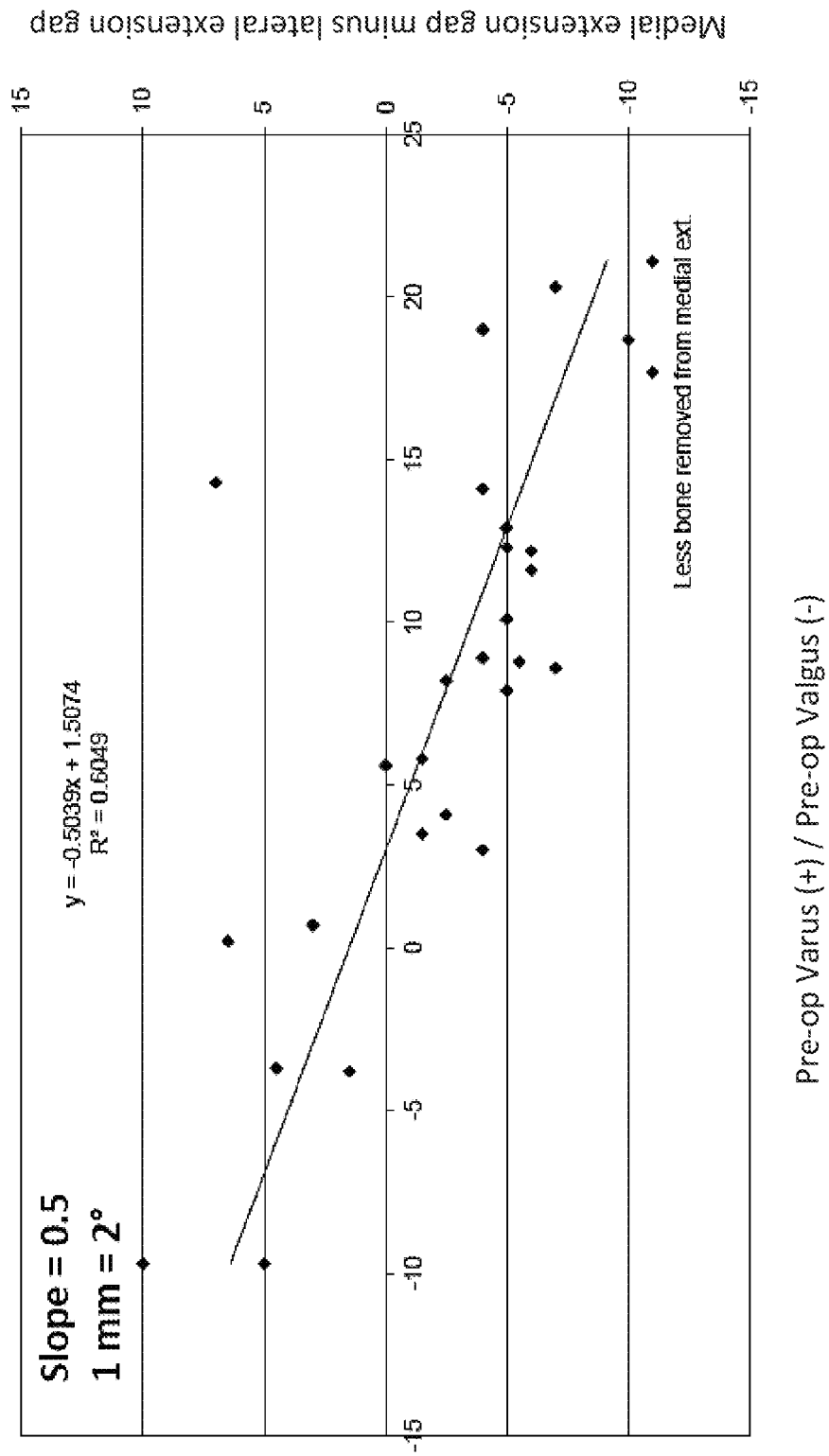
Figure 17:
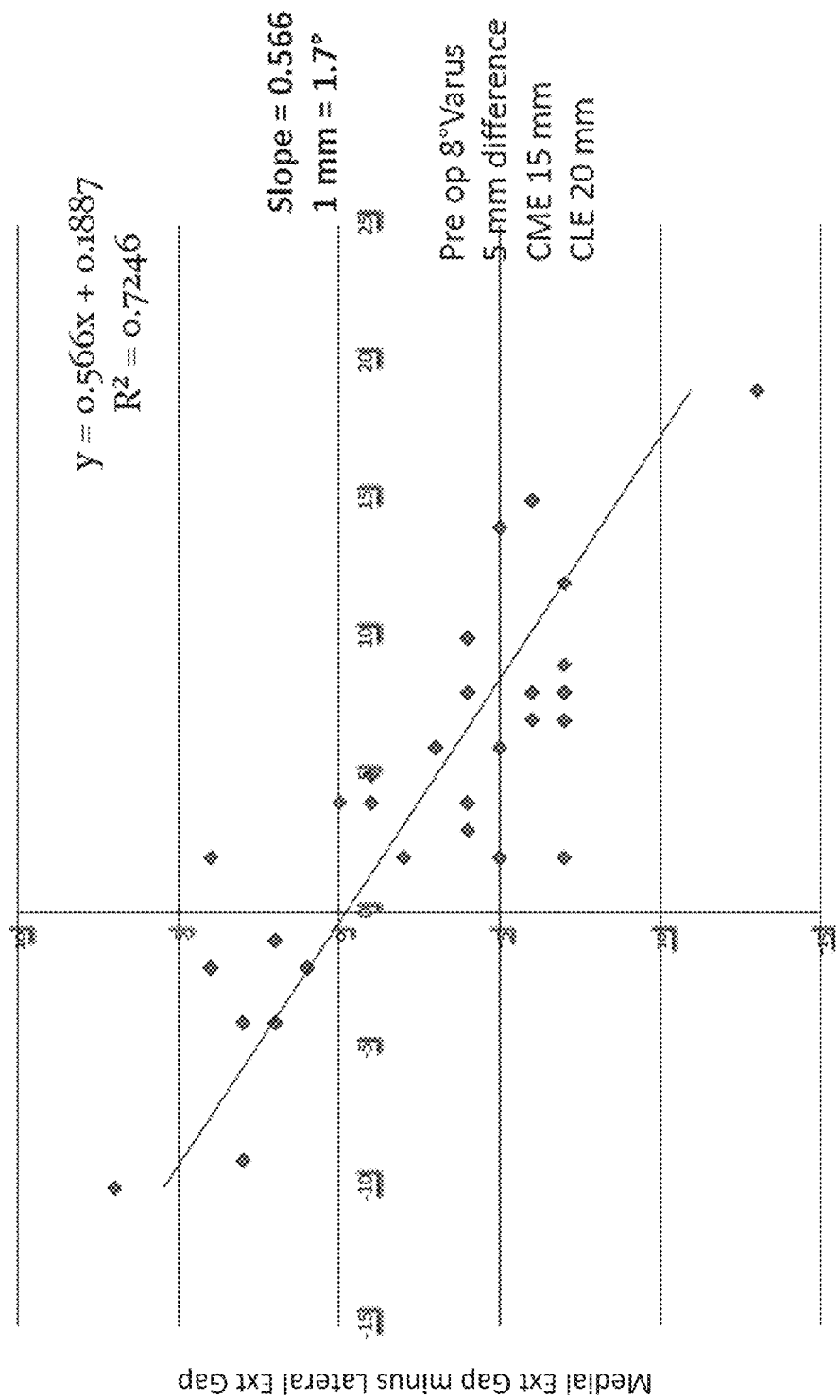

In various alternative embodiments, a surgeon might use an adjustable gap measurement tool to adjust the medial and lateral bars at different heights based on the proposed correction of a coronal or other alignment (not shown). Where the knee has a preoperative neutral alignment, such as shown in FIG. 13, the medial and lateral extension gaps 650 will typically be equal where the implant includes equal medial and lateral thicknesses. However, patients with a pre-operative coronal mal-alignment (i.e. a varus or valgus knee joint) might require a disproportionate amount of bone removal from the medial extension gap as compared to the lateral extension gap if they wished to have their malalignment reduced and/or corrected using a standard implant. For example, in a varus knee joint, the surgeon may remove less bone from the medial extension gap than the lateral extension gap (see FIG. 13). The difference in thickness of medial 660 and lateral 670 bone removed as compared to the prosthesis replacing the removed bone would desirably determine the degree of correction of the knee alignment (see FIG. 14). Depending upon the knee size and kinematics, each 1 mm difference in bone resection thickness of the medial side compared to the lateral side could correlate to an approximately 1.7 degree change in coronal alignment (see FIGS. 15-17). Therefore, if the patient has a pre-operative coronal alignment of 8 degrees of varus, the surgeon might expect the MEG to be approximately 5 mm less than the LEG. If the combined thickness of the implant is 20 mm, then the surgeon would expect the MEG to measure 15 mm and the LEG to measure 20 mm. The extension gap measurement tool could factor this 5 mm difference between the medial height and lateral height into the construction of this block. The difference between the heights of the medial and lateral bars on the flexion gap measurement block could be zero, could be equal to the difference between the medial and lateral bars on the adjustable extension gap measurement tool, or could be some percentage of the difference between the medial and lateral bars on an adjustable extension gap measurement tool.

In various embodiments, the surgeon might use an adjustable gap measurement tool to adjust the position(s) and/or orientation(s) of medial and lateral shim blocks (or cut guides, etc.) based on a proposed correction for patients with a pre-operative flexion contracture (i.e., the patient may be unable to fully straight their knee joint—not shown). Such patients might require additional bone removed in their extension gap than a patient with full pre-operative extension. Therefore, the surgeon attempting to alleviate and/or correct a pre-operative flexion contracture could position the TCB and the DFCB such that the distance between these two proposed cuts measured a few millimeters greater than the proposed thickness of the knee prosthesis in extension. If a patient lacked full flexion pre-operatively, the surgeon might position the TCB and APFCB such that the distance between these two proposed cuts measured a few millimeters greater than the proposed thickness of the knee prosthesis in flexion. By removing more bone, the ligaments (i.e., the MCL, LCL, ACL and/or PCL) would desirably have modified (i.e., more or less) laxity and possibly allow for more motion for the patient. Alternatively, the surgeon may decide to use a 10° flexion block. The 10° flexion block could be based off the implant thickness at 10 degrees of flexion and account for the change in the height from the rotation of the knee joint. The surgeon could also be given a 45° flexion block if there was concerns about mid-flexion instability. Both the 10° and 45° flexion block may be patient specific, if desired.

In another embodiment, the surgeon may use a gap measurement tool that could be used in conjunction with various shim block embodiments. Thin (i.e., 1, 2, 3, and/or 4 mm) shims may be used in place of the various gap measurement tools described herein, or may be added in addition to the gap measurement tools inserted proximate the knee joint on the medial and lateral side of the joint in both flexion and extension. These measurements could be added to the gap measurements to adjust the bone cuts as needed and give the surgeon a better feel for the ligament balancing. In various embodiment, such shims could allow the surgeon to "test" the balancing of the knee prior to moving the cutting blocks, with a desired thickness of the appropriate shim to balance the knee being equal to an amount the cutting should be moved to obtain the desired modification to the resection plan.

In alternative embodiments, any of the gap measurement tools contemplated herein may be designed to lock together to verify that the knee is in full extension and 90 degree of flexion for the extension gap measurement and the flexion gap measurement, respectively. For example, if one embodiment of a gap measurement tool is used to conduct balancing, but the patient is unable to straighten their leg, then the surgeon could be given a 10° flexion block to be placed, positioned, and/or integrated within the gap measurement tool. This 10° flexion block would be based off the implant thickness at 10 degrees of flexion and account for the change in the height from the rotation of the knee joint. The surgeon could also be given a 45° flexion block if there was concerns about mid-flexion instability. Both the 10° and 45° flexion blocks could be manufactured using patient specific measurements, if desired.

Figure 14:
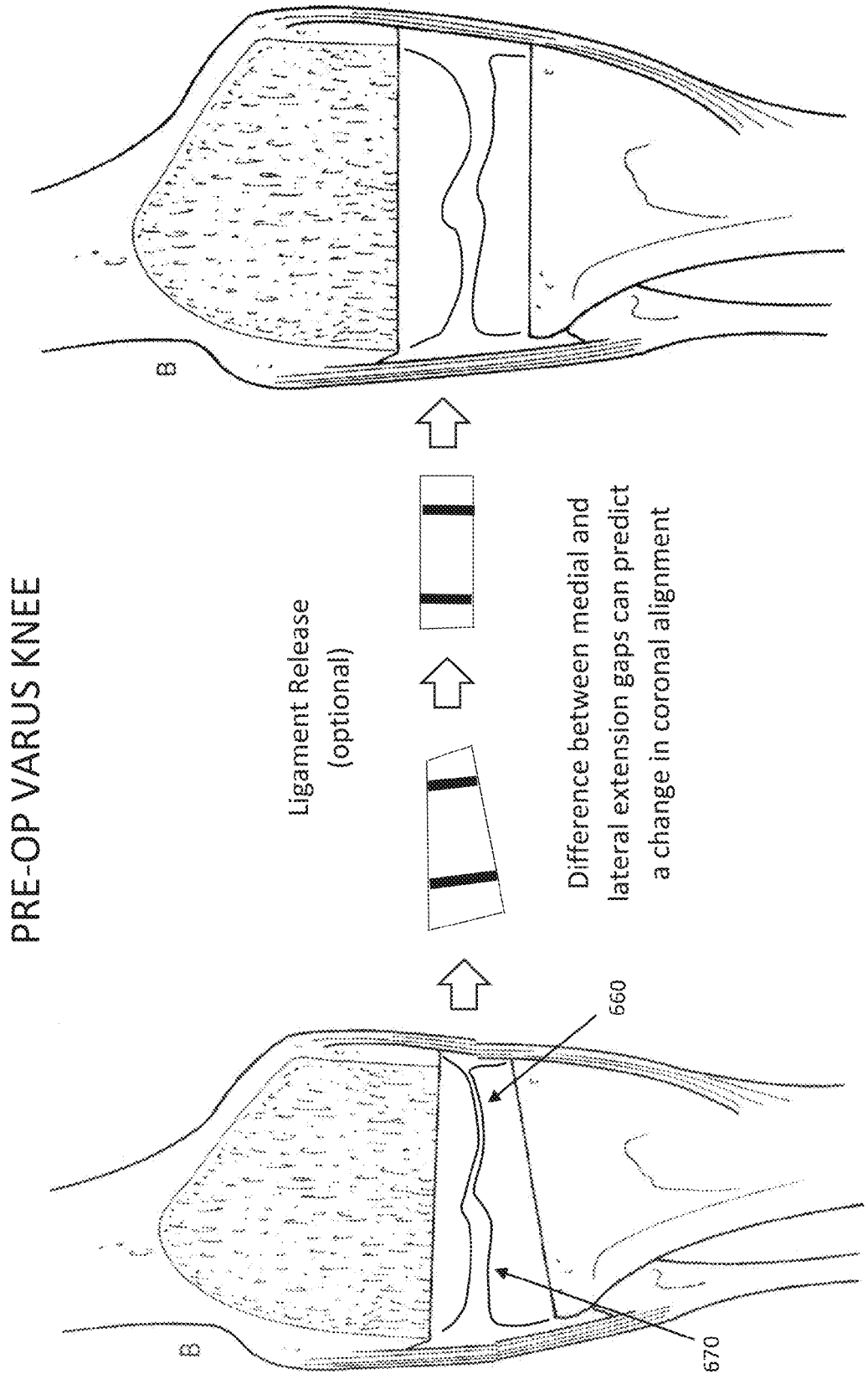
FIG. 14 depicts an embodiment of a knee joint having a pre-operative varus alignment.

In various embodiments, the gap measurement tool may be designed based on the patient's diseased state. For example, FIG. 14 depicts a knee joint having a femoral bone with a pre-operative translation deformity relative to the tibial bone. In a pre-operative ("pre-op") varus knee, the femur may translate medial to the tibial bone by a few millimeters (2-10 mm). When the articular surface of the femoral prosthesis resides on the tibial polyethylene, this translational deformity can be corrected if the implants are implanted correctly on the bones. The pre-op extension gap in a varus knee might desirably be a trapezoid, which can be transformed into a rectangular shape through ligament releases during surgery. This pre-op trapezoid in a varus knee could have a shorter side medially. When a medial release was preformed, then the shorter side (medial) could open up to match the longer side (lateral). Because the pre-op shape may be a trapezoid, the location of the measurement of the medial extension gap and lateral extension gap would be relevant to the analysis and correction. The width between the measurements could be relevant as well. The width of the blocks shown in FIGS. 3 through 6 could be patient specific. The positioning of where the blocks measure the medial and lateral extension gap could also be patient specific. Ideally, the various measurements described herein could be taken between the center of the medial femoral condyle articular surface and the center of the medial tibial plateau articular surface and between the center of the lateral femoral condyle articular surface and the center of the lateral tibial plateau articular surface, although other locations of measurement on the knee are contemplated as well. If a substantial amount of medial femoral translation were present, this translation could alter the measurements and, in various embodiments, will be factored into the measurements and/or assessments. In various embodiments, an analysis of the pre-operative imaging could include a shifting of the measurement blocks (i.e., by either or both of physically shifting the block position as well as designing the blocks to accommodate for measurement differences due to the anticipated shifted alignment) such that the measurements were made in the correct locations. This shifting could affect the height of the blocks shown in FIGS. 3 and 4. The change in height of the blocks could be determined by virtually implanting the femoral and tibial prosthesis in the correct location and working backwards to determine the vertical distance and horizontal distance (i.e., translation) of the medial extension gap and lateral extension gap. A computer-aid design and/or planning system could be used to set a point of rotation and rotate the height of the block according to how that horizontal translation would affect the vertical height along the trapezoid.

In an alternative embodiment, the surgeon could verify the measurements in flexion first and then extension, but the surgeon may elect (or it may be necessary) to remove the patient specific femoral jig to fully extend the knee joint to properly obtain and verify the gap measurements.

Any material known in the art can be used for any of the implant systems, tools and components described in the foregoing embodiments, for example including, but not limited to metal, metal alloys, combinations of metals, plastic, polyethylene, cross-linked polyethylene's or polymers or plastics, pyrolytic carbon, nanotubes and carbons, as well as biologic materials.

Any fixation techniques and combinations thereof known in the art can be used for any of the implant systems, tools and components described in the foregoing embodiments, for example including, but not limited to cementing techniques, porous coating of at least portions of an implant component, press fit techniques of at least a portion of an implant, pinning, ingrowth techniques, etc.

The above embodiments are applicable to all joints of a body, e.g., ankle, foot, elbow, hand, wrist, shoulder, hip, spine, or other joint.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions and claims provided herein.

What is claimed is:

1. A method of performing a total knee arthroplasty procedure comprising:
    making a primary incision near a knee joint of a patient;
    aligning a femoral jig with a femur of the knee joint;
    aligning a tibial jig with a tibia of the patient;
    positioning a spacer block at least partially between the femoral jig and tibial jig while at least a portion of the knee joint is undistracted, the spacer block including a medial height and a lateral height sized and configured to facilitate balancing of the knee by a surgeon, the medial and lateral heights being differing heights; and
    using a resection guide of at least one of the femoral or tibial jigs to guide a surgical cutting tool in cutting a resection plane on one of the femur or tibia.

2. The method of claim 1, wherein the spacer block is attached to the femoral jig.

3. The method of claim 1, wherein the spacer block is attached to the tibial jig.

4. The method of claim 1, wherein the tibial jig is attached to the tibia.

5. The method of claim 1, wherein the femoral jig is attached to at least one surface selected from the group consisting of an anterior femoral surface and a distal femoral surface.

6. The method of claim 1, wherein the medial height of the spacer block approximates a medial thickness of a knee implant for use in the total knee arthroplasty procedure.

7. The method of claim 1, wherein at least one of the medial and lateral heights is adjustable.

8. The method of claim 1, wherein the lateral height of the spacer block approximates a lateral thickness of a knee implant for use in the total knee arthroplasty procedure.

9. The method of claim 6, wherein the medial height of the spacer block approximates a medial flexed thickness of a knee implant for use in the total knee arthroplasty procedure.

10. The method of claim 6, wherein the medial height of the spacer block approximates a medial extended thickness of a knee implant for use in the total knee arthroplasty procedure.

11. The method of claim 1, wherein the spacer block modifies an alignment of the knee joint to at least partially correct a preoperative deformity of the knee joint.

12. A method of balancing a knee joint prior to resecting a bone surface during a total knee arthroplasty procedure, comprising:
    aligning a tibial referencing component with a tibia of the knee joint prior to resecting the knee joint;
    aligning a femoral extension referencing component with a femur of the knee joint prior to resecting the knee joint;
    positioning the knee joint in an extended position and inserting an extension spacer block between the tibial referencing component and the femoral extension referencing component, the extension spacer block being sized and configured to facilitate balancing of the knee joint in the extended position;
    positioning the knee joint in a flexed position;
    aligning a femoral flexion referencing component to the femur of the knee joint prior to resecting the knee joint;
    inserting a flexion spacer block between the tibial referencing component and the femoral flexion referencing component, the flexion spacer block being sized and configured to facilitate balancing of the knee joint in the flexed position; and
    resecting at least one bone surface of the knee after balancing the knee in the extended and flexed positions.

13. The method of claim 12, wherein the step of aligning a femoral extension referencing component with a femur of the knee joint prior to resecting the knee joint comprises attaching the femoral extension referencing component to the femur.

14. The method of claim 12, wherein the flexion spacer block includes medial and lateral heights that approximate a medial composite thickness and a lateral composite thickness of a knee arthroplasty implant that is implanted into the knee during the total knee arthroplasty procedure.

15. The method of claim 12, wherein the extension spacer block and the flexion spacer block are a single component.

16. The method of claim 1, wherein the step of positioning a spacer block at least partially between the femoral jig and tibial jig while at least a portion of the knee joint is undistracted comprises positioning the spacer block at least partially between the femoral jig and tibial jig while at least a portion of the femur is in contact with the tibia.

* * * * *